United States Patent
Moissl et al.

(10) Patent No.: US 11,676,712 B2
(45) Date of Patent: Jun. 13, 2023

(54) METHOD FOR CALCULATING OR APPROXIMATING A VALUE REPRESENTING THE RELATIVE BLOOD VOLUME AND DEVICES

(71) Applicant: Fresenius Medical Care Deutschland GmbH, Bad Homburg (DE)

(72) Inventors: Ulrich Moissl, Bad Vilbel (DE); Paul Chamney, Tring (GB); Volker Nier, Reichelsheim (DE); Peter Wabel, Darmstadt (DE); Sebastian Wieskotten, Riedstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 852 days.

(21) Appl. No.: 16/568,595

(22) Filed: Sep. 12, 2019

(65) Prior Publication Data
US 2020/0000404 A1    Jan. 2, 2020

Related U.S. Application Data

(63) Continuation of application No. 13/997,583, filed as application No. PCT/EP2011/006472 on Dec. 21, 2011, now Pat. No. 10,413,237.
(Continued)

(30) Foreign Application Priority Data

Dec. 23, 2010 (EP) .................................. 10015995

(51) Int. Cl.
*G16H 40/63* (2018.01)
*A61M 1/16* (2006.01)
(Continued)

(52) U.S. Cl.
CPC .......... *G16H 40/63* (2018.01); *A61B 5/0205* (2013.01); *A61B 5/0295* (2013.01);
(Continued)

(58) Field of Classification Search
CPC ....... A61M 1/14; G16H 20/40; A61B 5/0205; A61B 5/0295; A61B 5/4836;
(Continued)

(56) References Cited

U.S. PATENT DOCUMENTS 5,938,938 A    8/1999 Bosetto et al.
7,170,591 B2   1/2007 Ohishi et al.
(Continued)

FOREIGN PATENT DOCUMENTS

JP    H02-154741    6/1990
JP    2004-505708   2/2004
(Continued)

OTHER PUBLICATIONS

McMahon et al., "A non-invasive continuous method of measuring blood volume during haemodialysis using optical techniques," Medical Engineering and Physics Journal 18(2):105-109, 1996.
(Continued)

*Primary Examiner* — Puya Agahi
(74) *Attorney, Agent, or Firm* — Fish & Richardson P.C.

(57) ABSTRACT

The present invention relates to a method for calculating or approximating a value representing the relative blood volume (RBV) at a certain point of time, or a value representing the refilling volume of a patient that may be observed or found during or due to a blood treatment of the patient, the method involving considering one or more calculated or measured value(s) reflecting an overhydration level of the patient or an approximation thereof. It relates further to an apparatus and a device for carrying out the present inven-
(Continued)

tion, a blood treatment device, digital storage means, a computer program product, and a computer program.

14 Claims, 11 Drawing Sheets

Related U.S. Application Data

(60) Provisional application No. 61/426,522, filed on Dec. 23, 2010.

(51) Int. Cl.
| | |
|---|---|
| *G16H 20/40* | (2018.01) |
| *A61B 5/0205* | (2006.01) |
| *A61B 5/0295* | (2006.01) |
| *A61B 5/00* | (2006.01) |
| *A61M 1/30* | (2006.01) |
| *A61M 1/14* | (2006.01) |

(52) U.S. Cl.
CPC .......... *A61B 5/4836* (2013.01); *A61B 5/4848* (2013.01); *A61B 5/4875* (2013.01); *A61B 5/7225* (2013.01); *A61B 5/7278* (2013.01); *A61M 1/16* (2013.01); *A61M 1/1613* (2014.02); *A61M 1/30* (2013.01); *G16H 20/40* (2018.01); *A61M 1/14* (2013.01); *A61M 2205/52* (2013.01)

(58) Field of Classification Search
CPC ... A61B 5/4848; A61B 5/4875; A61B 5/7225; A61B 5/7278
See application file for complete search history.

(56) References Cited

U.S. PATENT DOCUMENTS

| | | | |
|---|---|---|---|
| 7,785,463 | B2 | 8/2010 | Bissler et al. |
| 7,788,038 | B2 | 8/2010 | Oshita et al. |
| 7,801,598 | B2 | 9/2010 | Zhu et al. |
| 2004/0057037 | A1 | 3/2004 | Ohishi et al. |
| 2006/0226079 | A1 | 10/2006 | Mori |
| 2008/0067132 | A1 | 3/2008 | Ross |
| 2009/0043222 | A1 | 2/2009 | Chetham |

FOREIGN PATENT DOCUMENTS

| | | |
|---|---|---|
| JP | 2004-097781 | 4/2004 |
| JP | 2006-288625 | 10/2006 |
| JP | 2008-504083 | 2/2008 |
| WO | WO 1999/019153 | 11/1991 |
| WO | WO 1992/019153 | 11/1992 |
| WO | WO 2006/002656 | 1/2006 |
| WO | WO 2006/002685 | 1/2006 |

OTHER PUBLICATIONS

International Search Report in International Application No. PCT/EP2011/006472, dated Jun. 4, 2012.
Bogaard et al., "Assessment of refill and hypovolaemia by continuous surveillance of blood volume and extracellular fluid volume," Nephrol Dial Transplant, 1994, pp. 1283-1287.
Drukker et at., "Replacement of Renal Function by Dialysis," Kluwer Academic Publisher, pp. 397-401, 2004.
Wabel et al., "Importance of Whole-Body Bioimpedance Spectroscopy for the Management of Fluid Balance", Blood Purification, vol. 27, pp. 75-80, XP007912086, ISSN: 0253-5062, DOI: 10.1159/000167013 [retrieved on Jan. 23, 2009].
Tattersall, "Bioimpedance Analysis in Dialysis: State of the Art and What We Can Expect," Blood Purification, Jan. 1, 2009, pp. 70-74, XP055081260, DOI: 10.1159/000167012 Retrieved from the Internet: URL:http://www.karger.com/Article/Pdf/167012 [retrieved on Sep. 26, 2013].
Japanese Search Report by Registered Searching Organization in Japanese Application No. 2013-545109, dated Oct. 19, 2015, 60 pages (with English translation).
Dasselaar et al., "Measurement of relative blood volume changes during haemodialysis: merits and limitations," Nephrol Dialysis Transplant, 2005, pp. 2043-2049.
Wizemann et al., "The mortality risk of overhydration in haemodialysis patients," Nephrol Dialysis Transplant, 2009, pp. 1574-1579.

METHOD FOR CALCULATING OR APPROXIMATING A VALUE REPRESENTING THE RELATIVE BLOOD VOLUME AND DEVICES

CROSS REFERENCE TO RELATED APPLICATIONS

This application is a continuation application of and claims priority under 35 U.S.C. § 120 to U.S. patent application Ser. No. 13/997,583, filed on Aug. 9, 2013, which is the national stage entry of International Patent Application No. PCT/EP2011/006472, filed Dec. 21, 2011, which claims priority from European Patent Application No. EP 10015995.3, filed Dec. 23, 2010 and the benefit of U.S. Provisional Patent Application No. 61/426,522. The disclosures of which are expressly incorporated herein in entirety by reference thereto.

FIELD OF INVENTION

The present invention relates to a method for calculating or approximating a value representing the relative blood volume at a certain point of time, or a value representing the refilling volume of a patient that may be observed or found during or due to a blood treatment of the patient. It further relates to an apparatus, a blood treatment device, digital storage means, a computer program product, and a computer program.

BACKGROUND OF THE INVENTION

During the extracorporeal treatment of blood, a decrease in the patient's blood volume (BV) and, hence, of the patient's relative blood volume (RBV) takes place. Its decrease depends on a number of parameters such as the absolute blood volume (BV) at the beginning of the treatment, an ultrafiltration rate (UFR) applied, if applied, and the like. Patients who are treated at an ultrafiltration rate (UFR) that has been set (too) high are likely to collapse during, e. g., dialysis because of the amount of fluid withdrawn from their body by the treatment. Patients who are treated at an ultrafiltration rate (UFR) that has been set (too) low are likely to unnecessarily spend time at the treatment site (hospital, clinic or even at home bound to the treatment machine), or, worse, to be sent home again without having reduced their overhydration (OH) level to an appropriate extent.

By means of the present invention, a method for calculating or approximating a value representing the relative blood volume (RBV) at a certain point of time, or a value representing the refilling volume (V_refill) of a patient that may be observed or found during or due to a blood treatment of the patient and/or for predicting a relative blood volume (RBV) with regard to a future time point or an absolute blood volume (BV) for a future time point is suggested. Also, an apparatus for carrying out the method according to the present invention is provided, as well as a device comprising the apparatus, digital storage means, a computer program product, and a computer.

In one aspect of the present invention, the method for calculating or approximating or predicting a value representing the absolute or relative blood volume or a value representing the refilling volume or predicting a future value (like RBV_end) comprises the step of considering one or more calculated or measured value(s) reflecting an overhydration level of the patient or an approximation thereof.

The patient can be either a human being or an animal. The patient may be sound or ill. The patient may be in need of medical care or not.

In another aspect of the present invention, the apparatus is configured to carry out the method according to the present invention.

In another aspect of the present invention, the blood treatment device comprises at least one apparatus according to the present invention.

In another aspect of the present invention, the digital storage means, in particular a disc, CD or DVD, flash memory, USB memory, or the like has electrically readable control signals which are able to interact with a programmable computer system such that a method according to the present invention will be executed.

In another aspect of the present invention, the computer program product has a program code stored on a machine readable data medium for executing a method according to the present invention when executing the program product on a computer.

In another aspect of the present invention, the computer program has a program code for the execution of a method according to the present invention when executing the program on a computer.

Embodiments can include one or more of the following features.

In certain embodiments according to the present invention, a point of time falls within a particular blood treatment session. In some embodiments, a point of time is a time when a blood treatment session has just come to an end.

In some embodiments according to the present invention, observing or finding a value is to be understood as measuring the value, as calculating the value or as deriving or determining it from other values of other parameters having influence on the value in question.

In certain embodiments according to the present invention, a value measured, observed, calculated or determined "due to a blood treatment" means a value of a parameter that has been changed due to the blood treatment. The value itself may be measured, observed, calculated or determined during, before or after a blood treatment session.

In some embodiments according to the present invention, a blood treatment may be a hemofiltration, an ultrafiltration, and/or a hemodialysis method.

In certain embodiments according to the present invention, "considering" a value means taking the value into account, in particularly in a subsequent mathematic computation.

This may take place by means of a mathematic formula referring to the considered value or comprising it or by establishing a mathematic relation between certain parameters or value including the "considered" one. In some embodiments according to the present invention, "considering" a value may be understood as using the value as an input value that is input into, for example, a (mathematic) formula, a computer, a control unit, a processor, or the like. The input value may originate from a measurement, a diagram, a spreadsheet, a table, or the like, for example.

In some embodiments according to the present invention, a value representing or reflecting a parameter, such as the absolute blood volume or the overhydration level of a patient, means either a value that directly or indirectly states or indicates that parameter.

For example, in certain embodiments according to the present invention, a value representing or reflecting the overhydration of a patient may be "3" followed by the dimension "liter", whereas a value that indirectly allows to derive or determine or approximate the overhydration of the patient may also be "3" having the dimension 'kilogram', or may be the abdominal girth, for example.

In some embodiments according to the present invention, a value representing or reflecting a parameter such as the absolute blood volume, the relative blood volume, the refilling volume or the overhydration of the patient is to be understood as the absolute blood volume, the relative blood volume, the refilling volume or the overhydration or as values thereof, e.g. noted in "liter".

In certain embodiments according to the present invention, an overhydration "level" may be understood as the amplitude or the extend of the overhydration. Both the term "overhydration" and the term "overhydration level" may relate to absolute or to relative values. If understood as a relative value, "overhydration" may be related to the normohydrated state of the patient who does not need fluid removal and/or whose kidneys work in the way they do in sound people.

In some embodiments according to the present invention, the overhydration or overhydration level is defined as the difference between the weight of the patient who needs excess water removal due to kidney problems and the patient's dry-weight. The dry-weight may be the patient's weight in a condition where no excess fluid exists or where no excess fluid has to be removed. The patient's dry-weight may be defined as in WO 2006/002685 A1. The respective disclosure of WO 2006/002685 A1 is hereby incorporated by way of reference.

In certain embodiments according to the present invention, an overhydration and an overhydration level (whereby these terms may be used interchangeably in some embodiments according to the present invention) relate to an overhydration or overhydration value of the patient right before starting the blood treatment session, at the beginning thereof, or during the blood treatment session.

In some embodiments according to the present invention, the overhydration or the overhydration level of a patient means the water or excess fluid accumulated within the body which the skilled person understands as fluid that should be removed—in parts thereof or as a whole—by means of the blood treatment.

In certain embodiments according to the present invention, the overhydration or the overhydration level equals the water or excess fluid accumulated within the body that would have been removed from the body by the kidneys if the kidneys worked properly.

In some embodiments according the present invention, some or all of the method steps are carried out by means of corresponding devices such as one or more processors. The devices are adapted and/or configured for carrying out the respective method steps.

In certain embodiments according to the invention, the method is a computer-implemented method.

In some embodiments according to the invention, the method is an automatic dialysis method.

In some embodiments according to the present invention, the method is an operator independent method for calculating or approximating or predicting a value representing the absolute blood volume, the relative blood volume or the refilling volume, or for controlling a blood treatment device.

In certain embodiments, the method according to the present invention encompasses considering the absolute start blood volume upon or before beginning the blood treatment for calculating or approximating or predicting either a value representing the relative blood volume or a value representing the refilling volume.

In some embodiments, for assessing the absolute start blood volume, at least one value reflecting the lean mass and at least one value reflecting the fat mass of the patient's body, and/or approximations thereof, are considered.

In certain embodiments of the present invention, the refilling volume (V_refill) is obtained by means of the following equation (which is below also addressed as equation (7)):

$$V_{\_refill} = a*UFV + b*\frac{UFT}{hb_{\_start}} + c*OH + d$$

In this equation, UFV, UFR and OH represent the ultrafiltration volume, the ultrafiltration rate and the overhydration level as used herein. "hb_start" is the concentration of hemoglobin in blood or any other suitable body fluid or tissue before or at the start of the treatment session, for example right after the start of the treatment.

In certain embodiments according to the present invention, parameter a equals 0.6015, b equals 0.0097, c equals 0.0223 and d equals 0.0442.

In some embodiments according to the present invention, one or more of a, b, c and d may be a negative value. In certain embodiments according to the present invention, one or more of a, b, c and d may equal zero.

Although the above noted values for a, b, c and d have been found to be helpful by the inventors to the present invention, the use of above equation is of course not limited thereto. Deviation in the values chosen for a, b, c and/or d are of course possible and also contemplated.

Of course, the equation given above may also be stated differently. As is obvious, it may have another structure as well, such as V_refill=a*UFV/Hb+b*OH+ . . . or the like.

In some embodiments, the refilling volume summed or added up over the whole treatment session may be calculated or approximated. In certain embodiments, values for the refilling volume may be calculated or approximated for certain time points. In the latter case, refilling volume values of interest may be obtained from, e. g., an exponential or exponential like extrapolation or intrapolation.

In some embodiments according to present invention, an end value of the relative blood volume arrived at an end of a blood treatment session without having caused intradialytic morbid events such as hypotonic episodes, crisis, collapse, convulsions, vomiting, sickness, nausea, or the like is predicted.

A hypotonic episode, or crisis, is in certain embodiments of the present invention defined as a subjectively felt indisposition related to low blood pressure or more or less sudden occurring blood pressure drop.

In some embodiments according to the present invention, a hypotonic episode, crisis, or collapse, is defined as a drop in blood pressure that exceeds a decrease of, e. g., 30 mmHg from the systolic blood pressure measured before or at the beginning of the treatment session (or another defined or predefined decrease in mmHg).

In certain embodiments according to the present invention, a hypotonic episode, crisis or collapse, is defined as an episode of the patient that requires medical assistance such as bringing the patient in a different posture, or stopping of the ultrafiltration, or supplying infusion of, e. g., NaCl, or the like.

In certain embodiments of the present invention, the method encompasses the step of controlling a blood treatment apparatus based on the relative blood volume calculated or approximated by means of the method according to the present invention. Similarly, in some embodiments of the present invention, the method encompasses the step of controlling a blood treatment apparatus based on the end value of the relative blood volume calculated or approximated or predicted by means of the method according to the present invention.

In certain embodiments of the present invention, the method encompasses the step of calculating or optimizing the treatment duration or the time a certain future blood treatment session lasts. The calculation or optimization is done by taking the relative blood volume or the end value of the relative blood volume into account that was gained from the method according to the present invention.

In some embodiments according to present invention, the method encompasses the step of correcting the relative blood volume by means of the patient's overhydration level—or under consideration thereof—to be a normalized or normohydrated relative blood volume (RBV_normohyd).

In certain embodiments of the present invention, the method encompasses the step of determining a target range of the relative blood volume intended to be met by the blood treatment at the end of a treatment session.

In some embodiments of the present invention, the apparatus is a controller or any (other) type of a computer.

In many embodiments of the present invention, the apparatus comprises corresponding devices such as one or more processor(s) for carrying out the method according to the present invention. The devices are adapted and/or configured for carrying out the respective method steps.

In certain embodiments of the present invention, the apparatus is or comprises a monitor.

In some embodiments of the present invention, the apparatus is configured to carry out the method according to any embodiment of the present invention.

In certain embodiments of the present invention, the apparatus comprises an output device for outputting results provided by carrying out the respective method.

In some embodiments of the present invention, the apparatus is configured to control a device for treating a patient's blood in relation to a value or target range representing the relative blood volume calculated or approximated or predicted by a method according to the present invention.

In certain embodiments, the control is such that the treatment session is terminated or interrupted—or the ultrafiltration rate (UFR) is adjusted such that the absolute blood volume or the relative blood volume (RBV) does not drop below a certain or predetermined value—once a calculated or approximated value or target range representing the relative blood volume is achieved or met by the treatment.

In some embodiments of the present invention, the apparatus is configured to control a device for treating a patient's blood such that the treatment session is terminated or interrupted once an end value of the relative blood volume is measured or calculated that has been predicted as an end value or target range of the relative blood volume. This may be a relative blood volume end value or target range that has been achieved or met without suffering any hypotonic episodes on the patient's part.

In certain embodiments of the present invention, the device according to the present invention is intended for treating a patient by means of dialysis.

In some embodiments according to the present invention, the device for treatment a patient is a machine for treating by means of hemofiltration, ultrafiltration, and/or hemodialysis.

In certain embodiments of the present invention, the apparatus is configured to control a device for treating a patient's blood such that the treatment session is terminated or interrupted once a threshold or a predetermined value of the patient's absolute blood volume has been detected or calculated.

In some embodiments according to the present invention the patient's absolute blood volume is determined during the blood treatment session by taking the relative blood volume determined during the blood treatment session into account.

In certain embodiments according to the present invention, the overhydration level is approximated, calculated or defined based on measured values and/or calculations reflecting the overhydration or the relative overhydration (relOH: overhydration (OH) over extracellular water (ECW)), etc. of the patient. As regards a definition of overhydration as used in certain embodiments of the present invention it is referred to WO 2006/002685 A1 where OH equals $a*ECW+b*ICW+c*$body weight. The respective disclosure of WO 2006/002685 A1 is hereby incorporated by way of reference. It is to be understood that the overhydration can be determined in different ways, all of which are known to the person skilled in the art. One of those methods comprises measuring of a dilution and calculate the overhydration based thereon.

In some embodiments according to the present invention, the overhydration level of the patient may be expressed by an age corrected overhydration or relative overhydration (relAEOH). In doing so, certain effects, e.g. due to age, can be eliminated for achieving more relevant values.

In some embodiments according to the present invention, the overhydration level of the patient is expressed by only one value, in particular a value having the dimension "liter".

In certain embodiments according to the present invention, the overhydration level is measured or approximated before dialysis or based on pre-dialysis values of the patient.

In some embodiments according to the present invention, pre-dialysis (pre-Dx) values or calculations may be data obtained immediately, i.e., moments or minutes before starting the next dialysis treatment. The present invention is, however, not limited to this. Data can also be obtained at any other point of time. Pre-Dx data appear to be more stable than others. Using them can therefore be of advantage.

In certain embodiments according to the present invention, a target range is defined in a diagram representing both the relative blood volume and the time. The target range may alternatively be a target area. The diagram may alternatively be a plot. The diagram may be a Cartesian coordinate system, also called a "rectangular coordinate system".

For determining the hydration or overhydration level also any appropriate monitor can be used, such as monitors based on bioimpedance or dilution techniques.

The monitor for obtaining data related to the hydration state or to the overhydration level can be a monitor as described in WO 2006/002685 A1. The respective disclosure of WO 2006/002685 A1 is hereby incorporated in the present application by way of reference. Of course, the present invention must not be understood to be limited to monitors determining the hydration state of the patient by bioimpedance measurements as is described in WO 2006/002685 A1. Other methods known in the art such as dilution measurements and also any other method known to the skilled person are also contemplated and encompassed by the present invention as well.

In some embodiments, the apparatus comprises furthermore an output device for outputting results provided by the apparatus. The output device may be a monitor having a display, a plotter, a printer or any other means for providing an output.

In certain embodiments, the hemoglobin (Hb) level, mass or concentration of the patient is calculated and/or measured. The measurement and calculations may be carried out by means of any method know in the art, using any device suitable therefor. In particular, in some embodiments, the respective data may be obtained by measuring hemoglobin concentration or mass from blood samples and/or from blood comprised in extracorporeal blood lines by means of an appropriate monitor. The measurements can be made by measuring the optical properties of the blood by optical sensors and/or by assessing acoustic properties like transit times and/or propagation velocities of ultrasonic pulses by ultrasonic sensors.

In certain embodiments, the apparatus comprises a monitor for measuring hemoglobin (Hb) concentrations (e. g., in [g/dl]) and/or for determining the blood volume by means of any monitor as described in "Replacement of Renal Function by Dialysis" by Drukker, Parson and Maher, Kluwer Academic Publisher, $5^{th}$ edition, 2004, Dordrecht, The Netherlands, on pages 397 to 401 ("Hemodialysis machines and monitors"), the respective disclosure of which is hereby incorporated by way of reference.

In some embodiments, the monitor is configured to measure the blood volume and/or the concentration of hemoglobin by means of measuring an electrical conductivity.

In certain embodiments, the monitor is configured to measure the blood volume and/or the concentration of hemoglobin by means of measuring an optical density.

In some embodiments, the apparatus is configured to measure the blood volume and/or the concentration of hemoglobin by means of measuring a viscosity.

In certain embodiments, the apparatus is configured to measure the blood volume and/or the concentration of hemoglobin by means of measuring a density.

In some embodiments, the apparatus comprises one or more corresponding probes and/or one or more sensors for carrying out the measurements such as electrical conductivity sensors, optical sensors, viscosity sensors, density sensors, and the like.

In certain embodiments, the device may be used for treating a patient by means of dialysis.

In particular embodiments, the device may be used for treating a patient (or the patient's blood) by hemofiltration, ultrafiltration, hemodialysis, etc.

The embodiments may provide one or more of the following advantages.

By means of the present invention, an end value for the relative blood volume that will most probably be tolerated by the patient without severe blood pressure drops, blood pressure crisis, or collapse (the latter also being referred to as morbid events herein) may be determined in advance or early during the treatment (e. g., if the knowledge of an initial or start Hb concentration is needed, a value that can be obtained only (shortly) after the treatment has been started) of the treatment session. This may provide for the possibility to control the dialysis machine based on a reliably predicted (RBV) basis. Hence, the (critical) relative blood volume calculated or predicted in advance can be advantageously be used as a target value for the relative blood volume. The dialysis machine can be controlled accordingly. For example, the machine can be programmed to stop ultrafiltration once the (critical) relative blood volume calculated or predicted has been determined or reached or to adjust the UFR in such a way that the target RBV is not under-run.

Further, in certain embodiments, the dialysis time or duration may advantageously be optimized in certain embodiments of the present invention, because being aware in advance of a predicted relative blood volume that will most probably be tolerated by the particular patient allows controlling the dialysis machine such that the predicted relative blood volume is achieved as quickly as requested by the circumstances.

Also, once the relative blood volume predicted in advance is reached, the dialysis procedure may be stopped since further ultrafiltration may appear to be neither needed nor recommended.

Further, for optimization of the dialysis time, the control described herein ensures in certain embodiments that a predetermined ultrafiltration volume is withdrawn from the patient within a minimal or optimal time.

Further, an ultrafiltration rate may be set once the duration of the dialysis has been set and the relative blood volume or the critical relative blood volume has been predicted or calculated by means of the present invention. The so determined ultrafiltration rate will not cause a severe drop in blood pressure (crisis, collapse, or the like).

Another advantage may be that the individual refilling properties of the patient in question can be assessed once the particular refilling volume is known. The refilling volume may be calculated as described above with respect to the present invention. An assessment of the individual refilling volume may contribute to discovering certain diseases or defects of the patient regarding his or her capillary conditions (e. g., the presence of a capillary leak syndrome); it may help to check the osmotic pressure (albumin concentration), and the like. Also, assessing of the individual refilling volume may allow for providing a more individual dialysis treatment. For example, the duration of the dialysis—which can at least partly be derived from refilling volume—may be adapted to the patient's particular needs. In any way, knowing the patient's refilling volume particularities may help to further adapt the treatment to the patient's particular needs.

Moreover, by adequate use of the equations shown above, the overhydration level expected for the beginning of the next treatment session may be estimated.

Hence, the method, the apparatus and further devices according to the present invention may advantageously solve the technical problem that is how to automatically stop an automatic blood treatment before the patient starts to suffer or feel uneasy. Another technical problem that may be advantageously solved by means of the present invention is how to shorten the time the blood treatment apparatus is needed for the treatment of the patient while achieving the intended or request removal of excess fluid (or overhydration).

BRIEF DESCRIPTION OF THE DRAWINGS

Other aspects, features, and advantages will be apparent from the description, figures, and claims.

DETAILED DESCRIPTION

Figure 1:
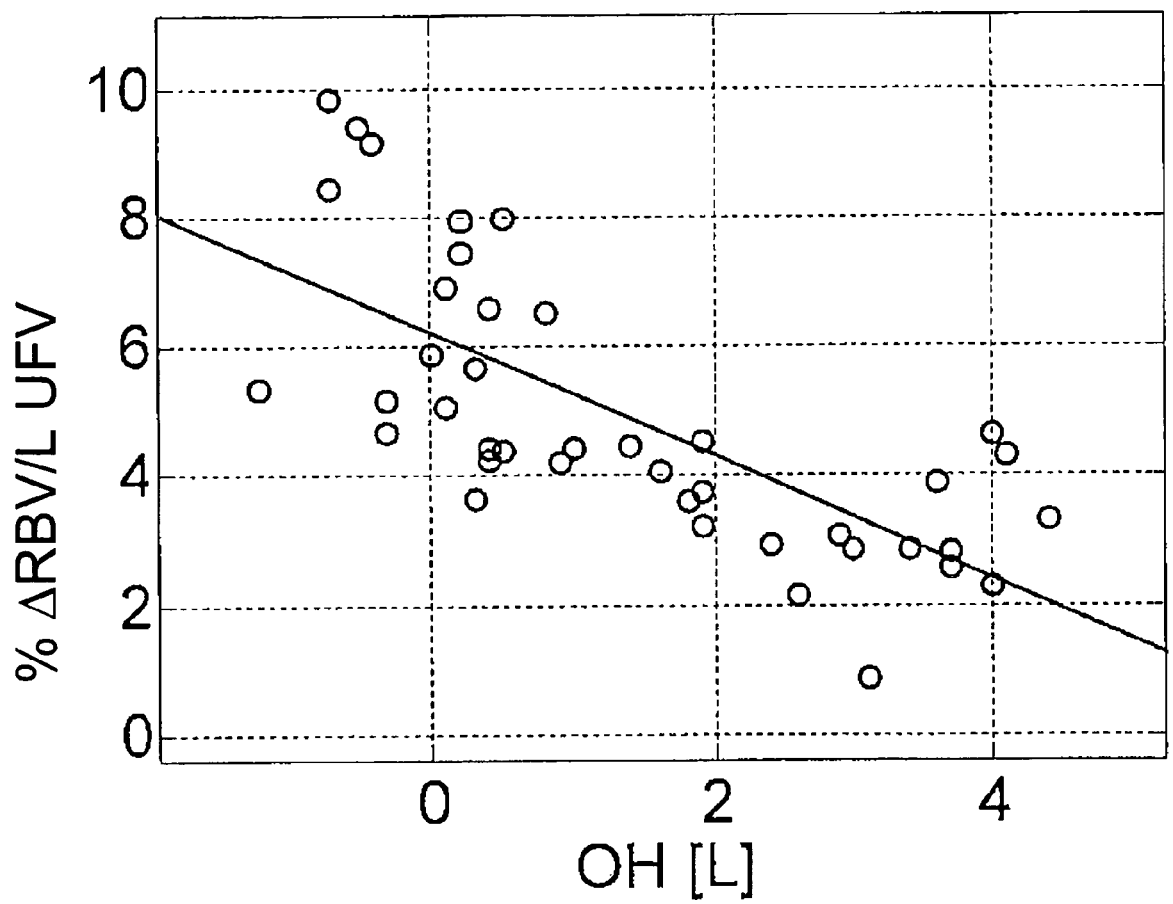
FIG. 1 shows the relative blood volume drop per liter ultrafiltration volume during dialysis over an initial overhydration (in liters)

FIG. 1 shows a correlation between the relative blood volume drop per liter ultrafiltration fluid in percent (short: % ARBV/UFV, UFV measured in liters [L]) during dialysis and an initial overhydration (in liters). The data of FIG. 1 have been gathered from a number of patients treated by ultrafiltration.

As can be seen from FIG. 1, the relative blood volume drop per liter ultrafiltration fluid is lower the higher the overhydration is before dialysis ("pre-Dx" overhydration).

Figure 2:
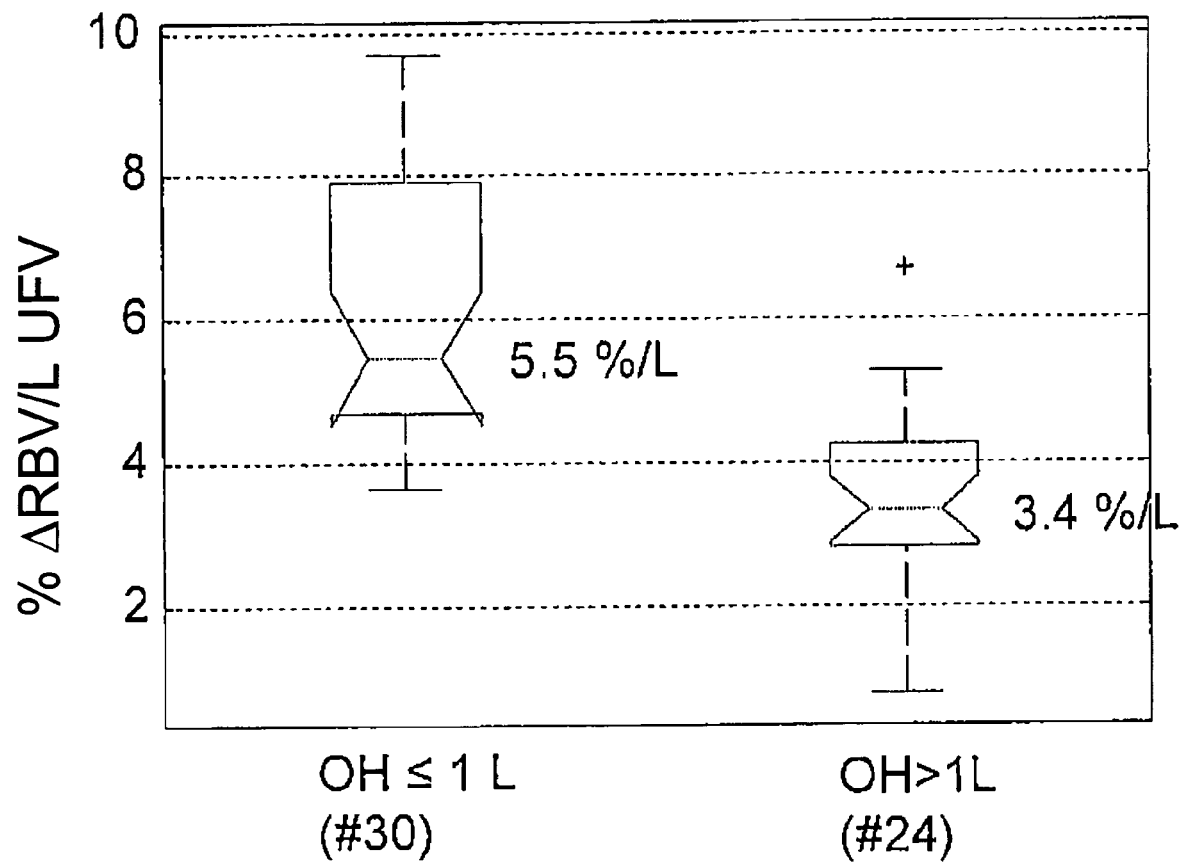
FIG. 2 shows data including those already used for the plot of FIG. 1 in another, classified presentation.

FIG. 2 shows data including those already used for the plot of FIG. 1 plus data of additional measurements. Another difference between FIG. 1 and FIG. 2 is the different way of representing the available data. In FIG. 2, the patients have been classified to have started dialysis with either an overhydration OH below one liter or above one liter.

As can be seen both from FIG. 1 and FIG. 2, the relative blood volume drop per liter ultrafiltration fluid (short: % ARBV/UFV [L]) is lower with patients (24 patients in number) who started dialysis with a higher overhydration, and vice versa. Further, as in FIG. 1, in FIG. 2 only data are shown that have been observed with patients from who more than 1.3 liters of ultrafiltration fluid have been withdrawn (UFV>1.3 liters).

As can be also seen from FIG. 1 and FIG. 2, for determining a target RBV value to be reached at the end of the treatment session, or for determining an optimized or critical RBV value (RBV_critical or RBV_min_tolerated), an overhydration level obviously is an important information and should hence be considered in setting an individual and optimal RBV_critical or RBV_min_tolerated.

The representations of FIG. 1 and FIG. 2 may help understand why certain patients suffered from relevant or severe blood pressure drops (hypotensive episode or crisis) during dialysis at different relative blood volume values in the past whereas others did not. One reason therefor may be the enhanced refilling (due to the higher amount of water comprised within the interstices) in overhydrated patients; another reason may be the enhanced absolute blood volume.

Also, FIGS. 1 and 2 help to understand, why a particular patient may collapse when a certain relative blood volume level or value is reached during a first dialysis session whereas he or she do not collapse when the same relative blood volume is reached during another, second dialysis session.

In the following, by way of example an approach reflecting said relevance of the overhydration before dialysis and its derivation are explained (with ABV being the drop, or change in general, of the absolute blood volume during dialysis):

$$\Delta BV = BV_{end} - BV_{start} = -UFV + V_{refill} \quad (1)$$

$$V_{refill} = BV_{end} - BV_{start} + UFV \quad (2)$$

$$V_{refill} = UFV - BV_{start} * \left(1 - \frac{RBV_{end}}{100}\right) \quad (3)$$

BV_start equals the normohydrated BV_0 plus the part of the excess fluid present in the blood compartment:

$$V_{refill} = UFV - \left(BV_0 + \frac{OH}{K_{Guyton}}\right) * \left(1 - \frac{RBV_{end}}{100}\right) \quad (4)$$

Assuming that BV_0 equals 0.1*LTM+0.01*ATM, with LTM being the muscle mass and ATM the fat mass of the patient in question, the refilling volume may be expressed as follows:

$$V_{refill} = \quad (5)$$
$$UFV - \left((0.1 + LTM + 0.01 * ATM) + \frac{OH}{K_{Guyton}}\right) * \left(1 - \frac{RBV_{end}}{100}\right)$$

Solving (5) for RBV_end:

$$RBV_{end} = \frac{100 * (V_{refill} - UFV)}{\left((0.1 * LTM + 0.01 * ATM) + \frac{OH}{K_{Guyton}}\right)} + 100 \quad (6)$$

In any equation presented within the present description, UFV stands for ultrafiltration volume, OH stands for the overhydration before starting the dialysis.

V_refill may be estimated, by way of example, as follows:

$$V_{refill} = a * UFV + b * \frac{UFR}{hb_{start}} + c * OH + d \quad (7)$$

As stated above, in certain embodiments according to the present invention, parameter a equals 0.6015, b equals 0.0097, c equals 0.0223 and d equals 0.0442. This is, however, not to be understood as limiting. Any other estimation is also contemplated.

The above stated values for parameters a, b, c and d have been empirically found. They have been step wisely analyzed for significance and cross validated.

Other approaches for estimating the refilling volume based on the UFV, UFR and OH are of course also contemplated. In those alternative approaches, hb_start may be comprised.

This is, however, not mandatory.

Also, the duration of the dialysis session T_dialysis may be calculated by dividing UFV by UFR.

Further, the overhydration OH may be expressed by a function f(UFV, UFR, LTM, ATM, hb_start, K_Guyton, RBV_end). The duration of the dialysis session T_dialysis may be expressed by a function f(UFV, OH, hb_start, LTM, ATM, K_Guyton, RBV_end). The ultrafiltration rate UFR may be expressed by a function f(UFV, OH, hb_start, LTM, ATM, K_Guyton, RBV_end, T_dialysis).

Figure 3:
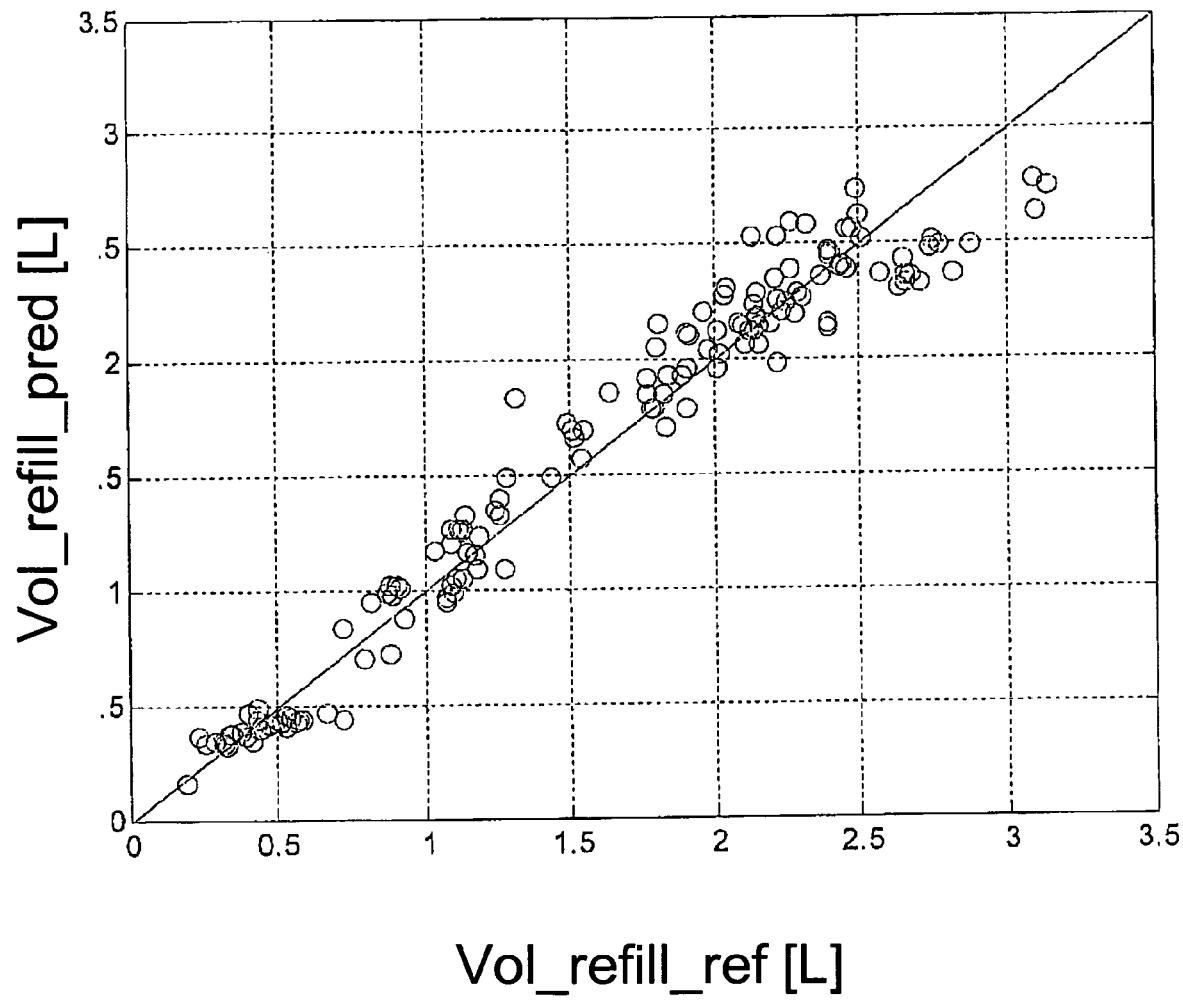
FIG. 3 shows a relation between the refilling volume as predicted over a refilling volume reference.

FIG. 3 illustrates a relation between the refilling volume (Vol_refill_ref in liter) as predicted by equation (5) over a refilling volume reference (Vol_refill_ref in liter). These reference values were calculated for the illustrated treatments by means of equation (5) and depicted along the x-axis, whereas the values found by means of equation (7) were depicted along the y-axis.

In the embodiment that corresponds to FIG. 3, it is believed that the expansion of the blood volume is proportional to the overhydraton OH because of a constant value for K_Guyton, and that LTM, ATM, etc. have been determined sufficiently correct.

As can be seen from FIG. 3, the predicted refilling volume (Vol_refill_ref in liter) corresponds quite well to the actually observed refilling volume reference (Vol_refill_ref in liter).

Figure 4:
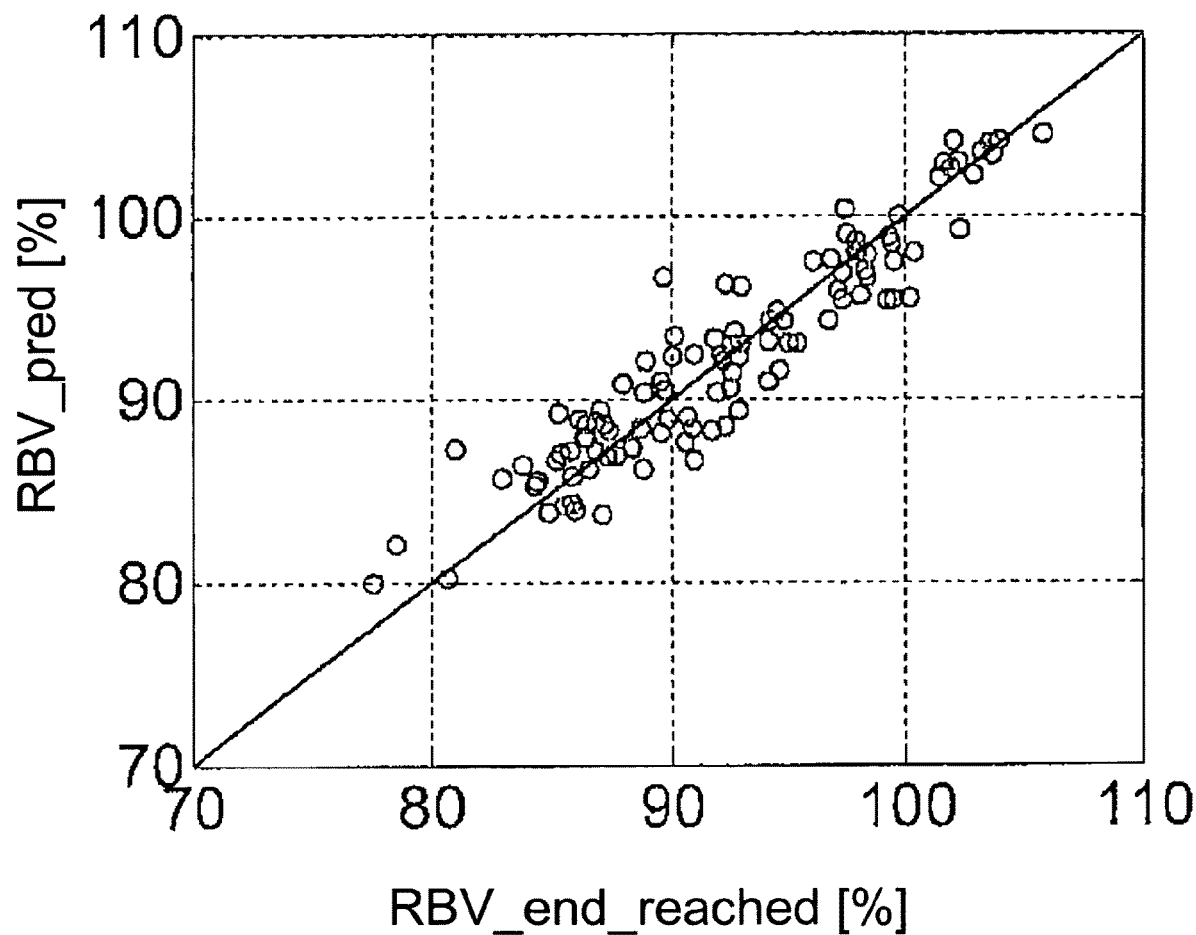
FIG. 4 shows the concordance between the predicted relative blood volume and the relative blood volume actually measured at the end of the treatment.

Similarly, what has been demonstrated above with reference to FIG. 3 may also be observed in FIG. 4. The data plotted in FIG. 4 show that the predicted relative blood volume RBV_pred [in %] corresponds very well to the relative blood volume (RBV_end_reached [in %] reached once the ultrafiltration volume that was set by the physician before starting the treatment was withdrawn from the blood.

The standard deviation (SD) of the values shown is +/−2.2%. Each point shown in FIG. 4 represents one complete treatment session (in total, 109 measurements).

It is noted that the data shown in the figures discussed here were achieved during or by treatments that were carried out with a constant ultrafiltration rate applied. It is, however, contemplated that the idea of the present invention may also be embodied with ultrafiltration rates that are not kept constant during treatment.

Figure 5:
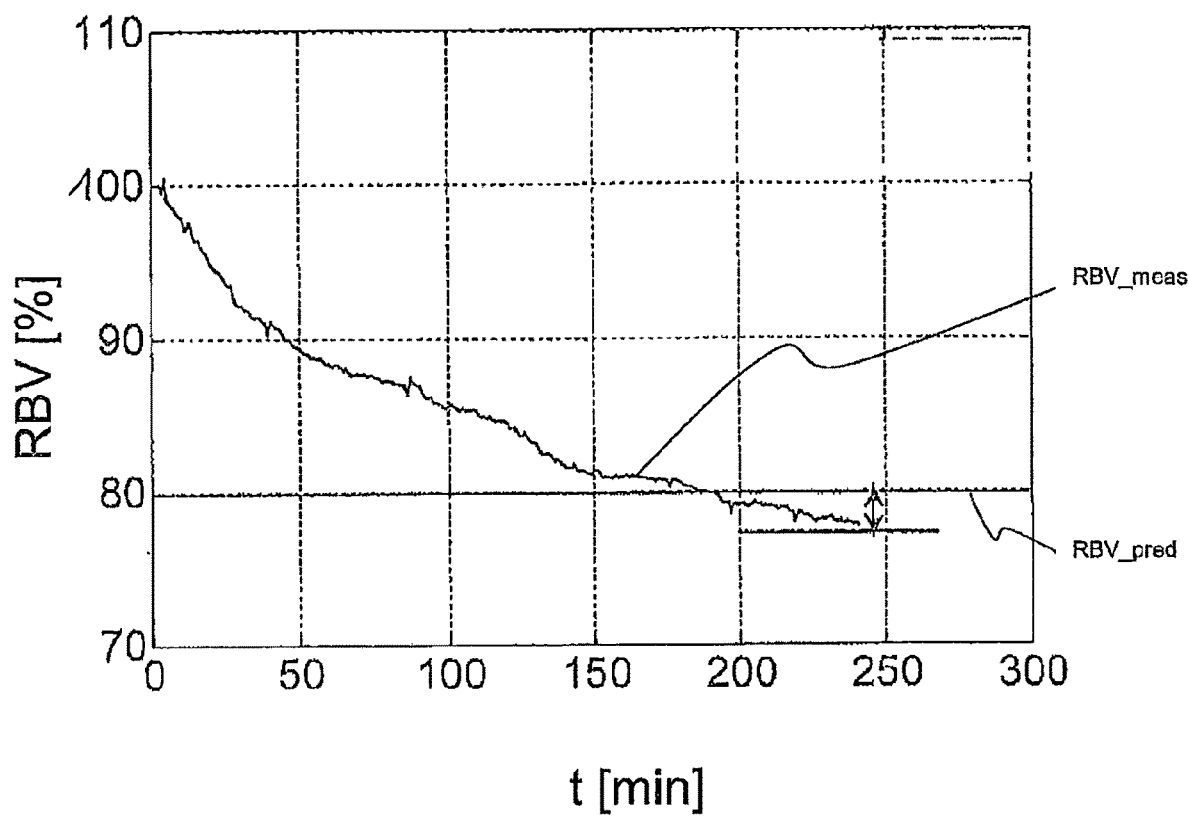
FIG. 5 shows the relative blood volume as measured in the course of one single treatment session.

FIG. 5 represents the relative blood volume as measured (RBV_meas in [%]) in the course of one single treatment session. The relative blood volume (RBV) is illustrated over the duration of the session (time t in minutes).

Reference sign RBV_meas depicts the actual, measured course of the relative blood volume over time t. Reference sign RBV_pred shows the predicted relative blood volume. As can be seen, there is hardly any deviation (the deviation is represented by the arrow of FIG. 5) between the predicted and the matter-of-fact end relative blood volume. In any case, controlling the dialysis apparatus based on the in advance calculated or predicted predicted relative blood volume RBV_pred would not have caused any hypotensive crisis with regard to the particular treatment session reflected in FIG. 5.

Figure 6:
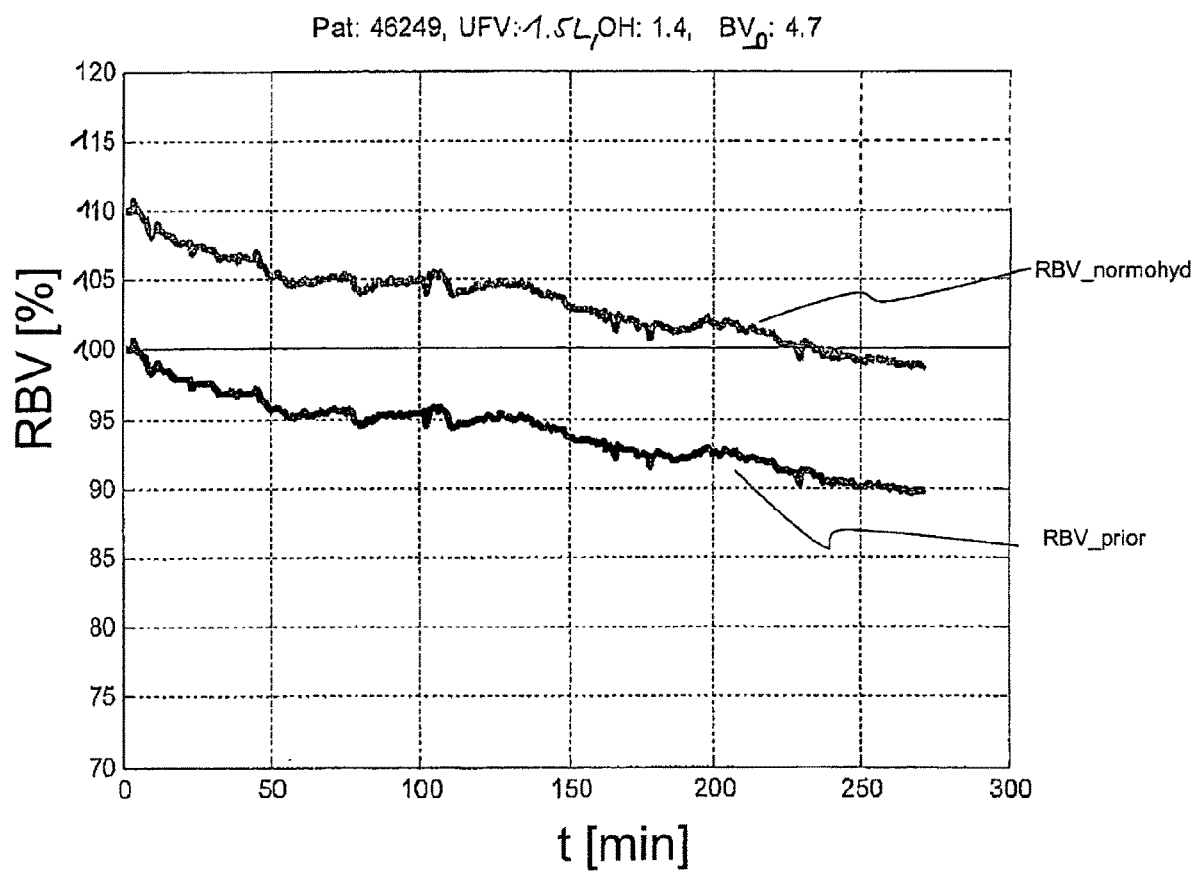
FIG. 6 shows another way of how a blood treatment machine may be controlled according to certain embodiments of the present invention.
Figure 7:
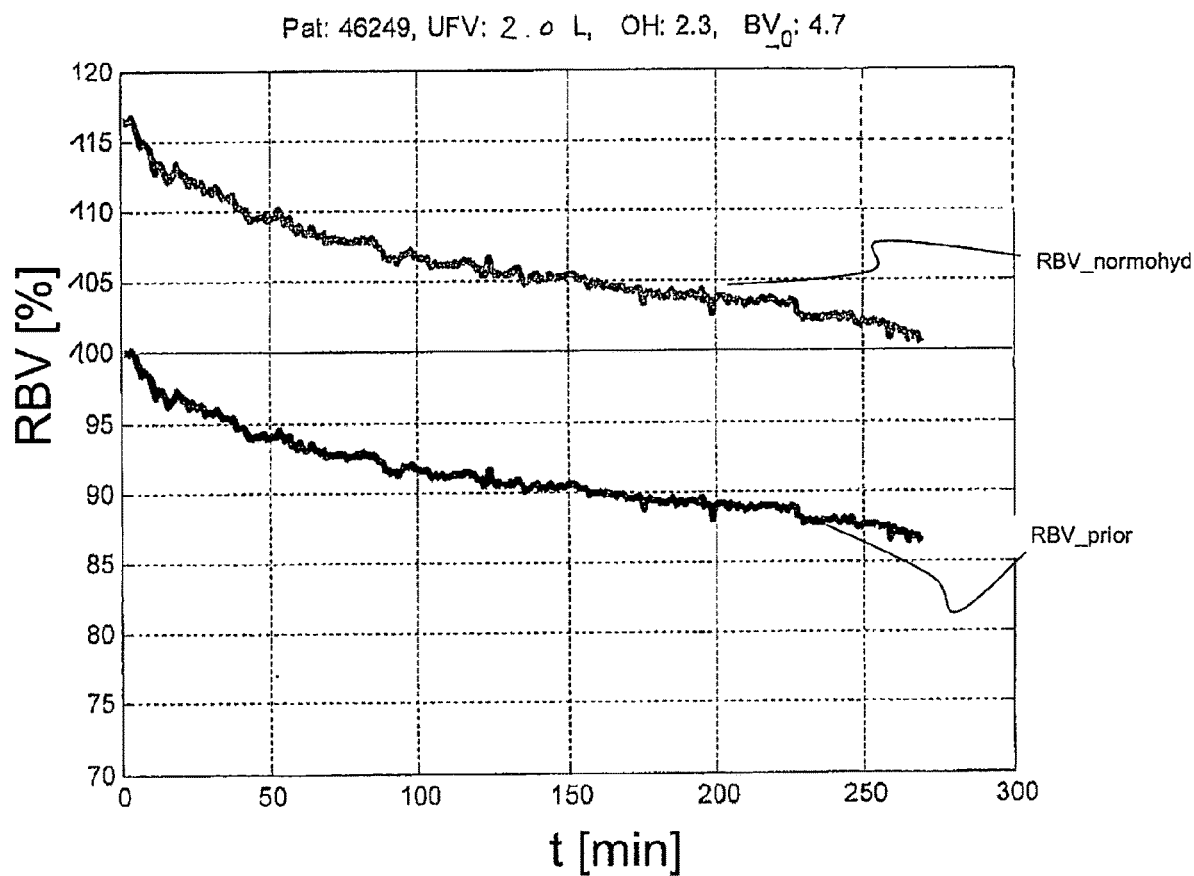
FIG. 7 shows another way of how a blood treatment machine may be controlled according to certain embodiments of the present invention.
Figure 8:
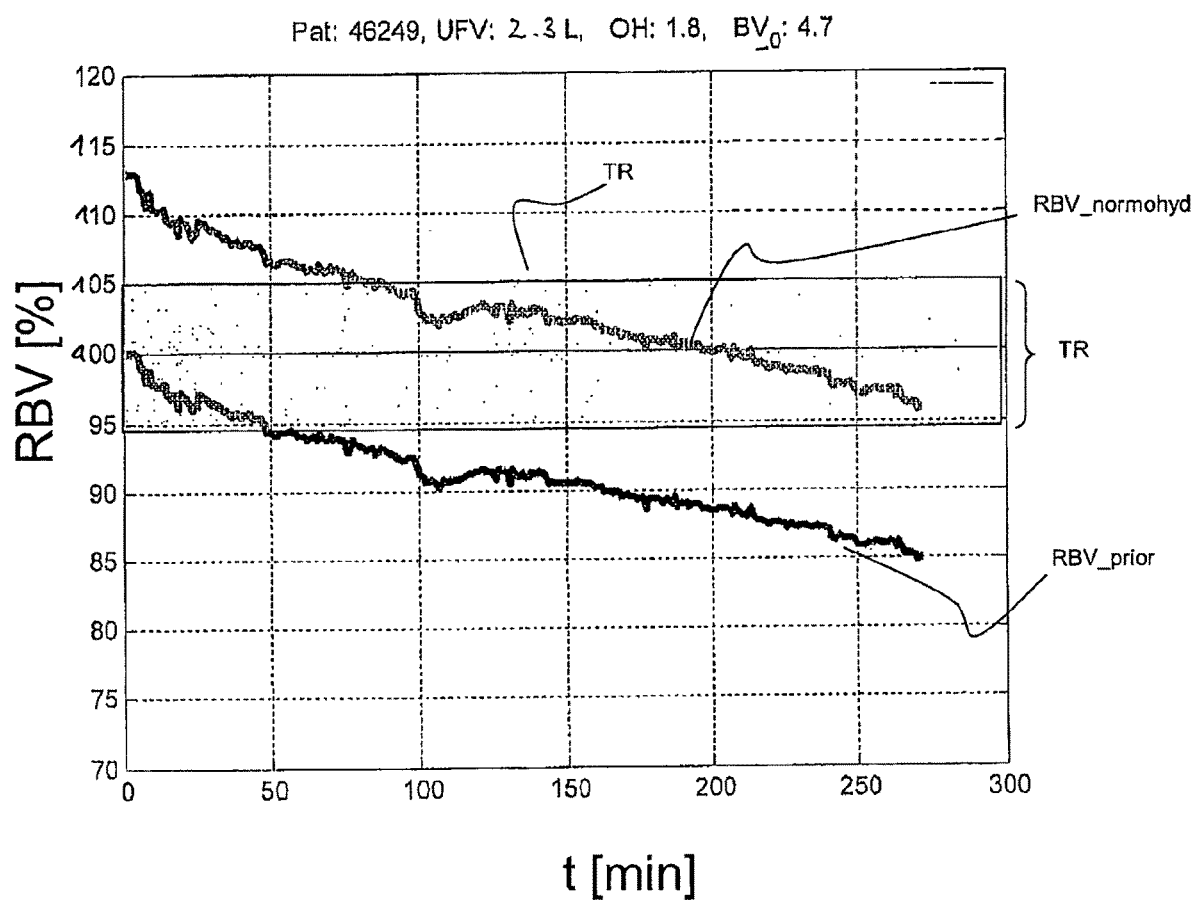
FIG. 8 shows another way of how a blood treatment machine may be controlled according to certain embodiments of the present invention.

FIG. 6 to FIG. 8 are intended to explain further ways of how a blood treatment machine may be controlled according to certain embodiments of the present invention. In FIG. 6 to FIG. 8, the course of the relative blood volume RBV is illustrated over time t [min]. The data have been recorded during three different dialysis treatments of patient "46249" who had a constant, normohydrated absolute start blood volume BV_0 of 4.7 liter at the beginning of each treatment session. The patient's overhydration OH differed between 1.4 (FIG. 6) and 2.3 liter (FIG. 7). In these three sessions, an ultrafiltration volume between 1.5 (FIG. 6) and 2.3 liter [L] (FIG. 8) was removed, respectively.

In each of FIGS. 6 to 8, graph RBV_prior shows the development of the relative blood volume during the time that has passed since the beginning of the treatment. With respect to the present invention, the term RBV_prior reflects the results of a blood volume monitor measurement as is carried out to date in the prior art. RBV_prior (that could, therefore, also be called RBV classical or RBV standard or the like and that is calculated as BV(t)/BV_start) reveals the relative blood volume as measured. RBV_prior is, however, not a normohydrated blood volume. As can be seen from FIGS. 6 to 8, the treatment starts with a relative blood volume RBV_prior of 100% and ends at an reduced relative blood volume between 85 and 95%. Hence, as can easily be seen from these figures, the relative blood volume measured at the end of the treatment may differ from treatment to treatment, even though the same amount of fluid was reduced at each treatment, because the relative blood volume was determined relative to different absolute values for the blood volume at the beginning of the treatment. For that reason, controlling a dialysis machine (or adequately setting the ultrafiltration rate or volume) based on a critical or end value of the relative blood volume set or determined in advance may be difficult in the prior art with certain patients—in contrast to what can be achieved by means of the present invention.

According to some embodiments of the present invention, a relative blood volume RBV_normohyd, (here also called a normohydrated relative blood volume) that is "corrected" for the overhydration found in the patient at issue before the dialysis session is used for controlling the dialysis machine.

The normohydrated relative blood volume RBV_normohyd can be calculated, e.g., as follows:

$$RBV_{normohyd}(t) = \frac{BV\_absolut\_startDialysis}{BV\_0} * RBV_{prior}(t) = \frac{BV_0 + \frac{OH}{K\_Guyton}}{BV\_0} * RBV_{prior}(t) \qquad (8)$$

wherein BV_absolute_startDialysis stands for the absolute blood volume at the beginning of the treatment session, and wherein BV_0 stands for the absolute blood volume corrected for the fluid contribution to the vessel system due to the overhydration. The Guyton factor K_Guyton indicates what portion of the overhydration is comprised within the vessel system.

That way, an overhydrated patient would start his or her dialysis treatment with a normohydrated relative blood volume RBV_normohyd that is higher than 100% as can be seen from FIGS. 6 to 8. In the example of FIG. 6, the patient started treatment with an overhydration of 1.4 liters. 1.5 liters were removed. The actual blood volume BV_absolute_start Dialysis was 4.7 liters plus 1.4/3 equals 5.2 liters. The normohydrated absolute start blood volume BV_0 was 4.7 liters. The Guyton factor K_Guyton indicating what portion of the overhydration is comprised within the vessel system was assumed to be 3. Hence, the patient started with a fictive relative blood volume or normohydrated relative blood volume of 110% (5.2 liters/4.7 liters) with the dialysis session. When the dialysis comes to an end, the normohydrated relative blood volume RBV_normohyd is 100%. The absolute blood volume of 4.7 liters has been restored by then. The overhydration has been reduced to 0 liter by then. Keeping in mind that the ultrafiltration volume UFV was 1.5 liters in the present treatment, the patient's refilling volume was 4.7 liters minus (5.2 minus 1.5 liters) equals 1 liter.

As is readily understood from FIG. 6 to FIG. 8, controlling the dialysis based on the normohydrated relative blood volume RBV_normohyd is quite easy as it suffices to stop the ultrafiltration once a normohydrated relative blood volume RBV_normohyd of 100% is reached in the respective treatment session, assuming no refilling takes place after dialysis. This can be achieved by running at a very low UFR at the end of the treatment, so that vascular and interstitial spaces approach more or less equilibrium (in terms of filtration pressures). As is also obvious from the above, the stop value of 100% may remain unaltered for the normohydrated relative blood volume RBV_normohyd, both in every single treatment and irrespective of what particular patient is treated. Controlling the machine as proposed here may reduce the programming effort.

FIG. 7 reflects another treatment of the same patient. Due to the higher overhydration OH of 2.3 liters (when compared to the treatment of FIG. 6, it was 1.4 liters there), the dialysis of FIG. 7 starts at a normohydrated relative blood volume RBV_normohyd of 117% (compared to 112% in FIG. 6).

Additionally, as is indicated in FIG. 8, it may be contemplated to set a target range TR for the normohydrated relative blood volume RBV_normohyd that is to be met at the end of the treatment.

For example, the target range TR may be set 3%, 5% or more below and/or above the 100% envisaged.

Further, the target range TR does not necessarily cover an end value of the normohydrated relative blood volume RBV_normohyd that is always 100%. The range may also be used to cover an area around any desired end value for the treatment in question. Hence, under certain circumstances, a target range may relate to an end value of, e. g., 90% or 95%, depending on the patient.

Figure 9:
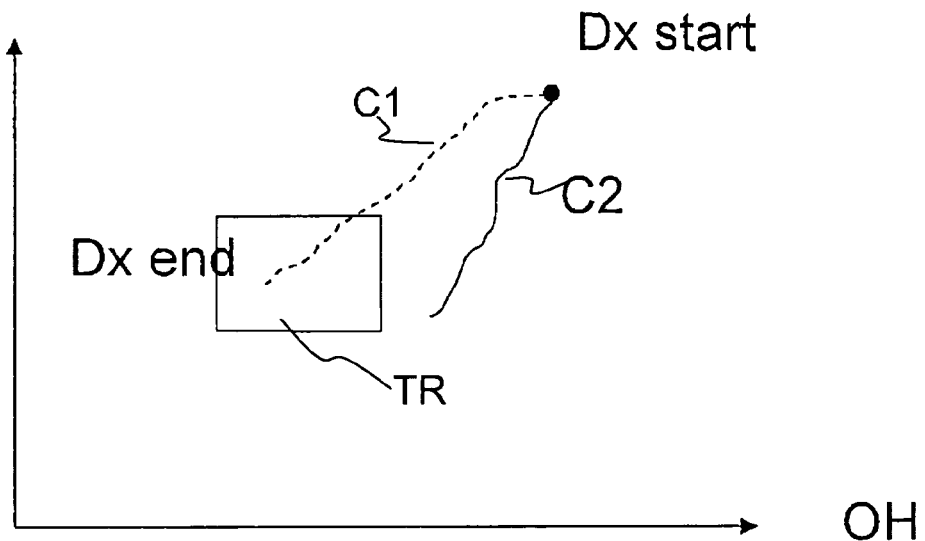
FIG. 9 shows a normohydrated relative blood volume over the overhydration.

FIG. 9 shows the normohydrated relative blood volume RBV_normohyd depicted over the overhydration OH. Further, in FIG. 9, a start point Dx_start and an end point Dx_end for the dialysis treatment at issue are illustrated. A target range TR is set that indicates an area in the plot of FIG. 9 that is acceptable for the values of both the normohydrated relative blood volume RBV_normohyd and the overhydration OH at the end of the treatment.

It is noted that instead of OH as described above, a time averaged value of OH (TAFO, a mean between pre and post overhydration values) can be used for embodying the idea of the present invention, including the idea described with regard to FIG. 9 without being limited thereto.

In FIG. 9, two possible way of treatment or of controlling the dialysis machine are depicted as C1 and C2.

At end point C2 the patient has a normohydrated blood volume BV; however, the patient is still overhydrated. In consequence, a rebound of water from the interstices into the blood vessels has to be expected as the end point C2 will still rise in the illustration of FIG. 9 after the treatment (OH will stay at a constant level, but the blood volume BV will rise).

On the other hand, at end point C1 there is no rebound because the patient is not overhydrated, and also because the distribution of water between blood volume BV and interstices has found an equilibrium.

In certain embodiments, a control according to the present invention is contemplated as follows:

After 10 to 30 minutes after the begin of the treatment the direction of the curve (e. g. in a representation like that of FIG. 9) is determined. It is assessed whether or not the curve will most probably meet the target range. This assessment may be done by mere observation on the monitor (naked eye) or via a more sophisticated approach such as an algorithm. If it is assumed that the curve will end within the target range, nothing has to be done. However, in case the curve declines too steeply, as is the case with C2, this may indicate that the blood volume decreases too quickly or strongly, both of which may indicate that the refilling is restricted or limited. Hence, it might be wise to limit the ultrafiltration rate UFR and to prolong the duration of the diayisis treatment. That end, the curve may eventually meet the target range in a "flat manner".

In contrast, in case the curve of FIG. 9 runs above of the target range, the treatment control may increase the ultrafiltration rate UFR until the curve heads towards the target range again and/or is believed to meet the target range or to end therein.

In certain embodiments of the control method or the devices for carrying out the methods, the manipulated variables comprise in first place the ultrafiltration rate and/or the duration of the dialysis treatment. Besides, additional means such as salt boli and their administration for enhancing the refilling are contemplated.

Figure 10:
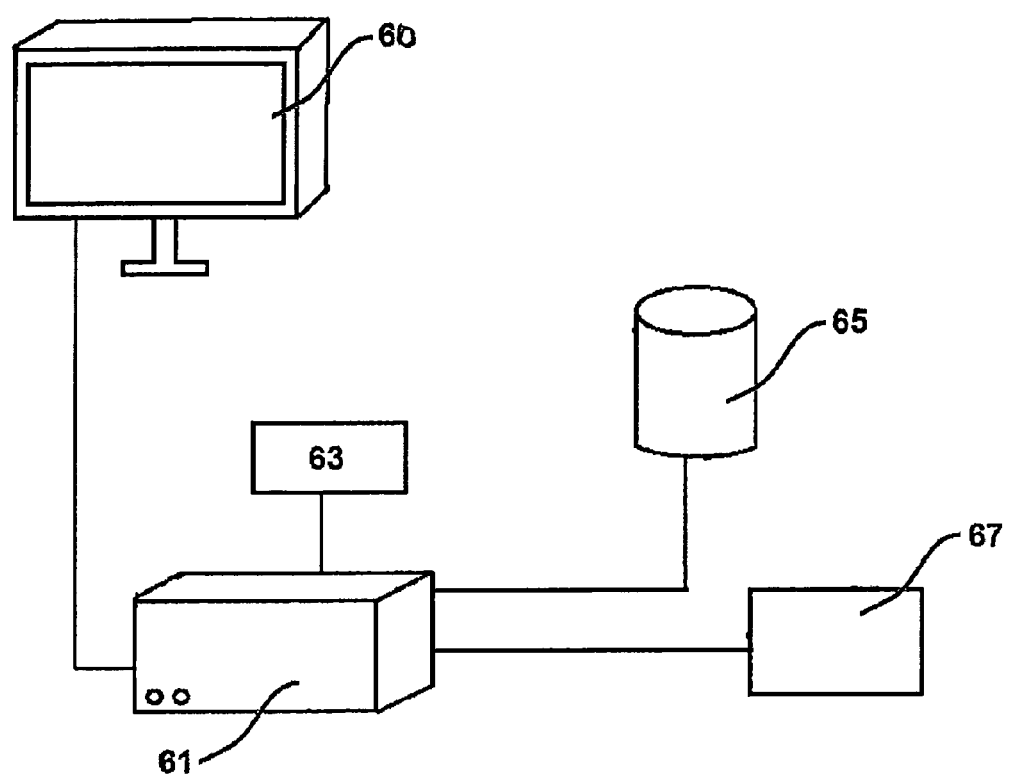
FIG. 10 shows a first apparatus comprising a controller for carrying out the method according to the present invention.

FIG. 10 shows an apparatus 61 comprising a controller 63 configured to carry out the method according to a first embodiment of the present invention. The apparatus 61 is optionally connected to an external database 65 comprising the results of measurements and the data needed for the method according to the present invention. The database 65 can also be an internal means of the apparatus 61. The apparatus 61 may optionally have means 67 for inputting data into the controller 63 or into the apparatus 61 itself. Such data may be information about the ultrafiltration rate set, the ultrafiltration volume planned to be eliminated from the body, etc., or approximations thereof. The results provided by the controller 63 and/or the apparatus 61 can be displayed on a monitor 60 or plotted by means of a—in FIG. 10 not displayed but optionally also encompassed—plotter or stored by means of the database 65 or any other storage means. The database 65 can also comprise a computer program initiating the method according to the present invention when executed.

Figure 11:
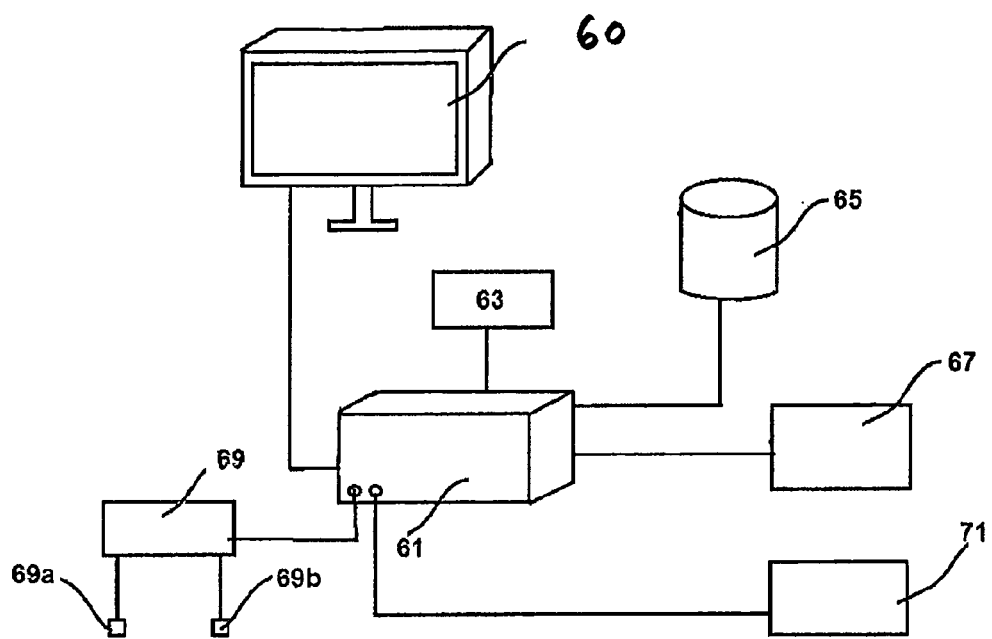
FIG. 11 shows a second apparatus comprising a controller for carrying out the method according to the present invention.

As can be seen from FIG. 11, for corresponding measurements, the apparatus 61 according to a second embodiment can be connected (by means of wires or wireless) with a bioimpedance measurement means 69 as one example of a means for measuring or calculating the overhydration, the lean mass, the fat mass or other parameters of the body or approximations thereof. Generally, the means for measuring or calculating can be provided in addition to the external database 65 comprising the results of measurements and the data needed for the method according to the present invention, or in place of the external database 65 (that is, as an substitute).

The bioimpedance measurement means 69 can be capable of automatically compensating for influences on the impedance data like contact resistances.

An example for such a bioimpedance measurement means 69 is a device from Xitron Technologies, distributed under the trademark Hydra™ that is further described in WO 92/19153, the disclosure of which is hereby explicitly incorporated in the present application by reference.

The bioimpedance measurement means 69 may comprise various electrodes. In FIG. 7, only two electrodes 69a and 69b are shown which are attached to the bioimpedance measurement means 69. Additional electrodes are, of course, also contemplated.

Each electrode implied can comprise two or more ("sub"-)electrodes in turn. Electrodes can comprise a current injection ("sub"-)electrode and a voltage measurement ("sub"-)electrode. That is, the electrodes 69a and 69b shown in FIG. 11 can comprise two injection electrodes and two voltage measurement electrodes (i.e., four electrodes in total).

Generally spoken, the apparatus according to the present invention can be provided with means such as weighing means, a keyboard, a touch screen etc. for inputting the required data, sensors, interconnections or communication links with a lab, any other input means, etc.

Similarly, the apparatus 61 may have further means 71 for measuring or calculating means for obtaining a value reflecting the overhydration and/or for obtaining values reflecting the mass, the volume or the concentration of Hb that can be provided in addition to the external database 65 or in place of the external database 65 (that is, as an substitute).

The means 71 can be provided as a weighing means, a keyboard, touch screen etc. for inputting the required data, sensors, interconnections or communication links with a lab, an Hb concentration probe, any other input means, etc.

Below, an exemplary way is described of how an apparatus according to the present invention works that is configured to control a device for treating a patient's blood such that the treatment session is terminated or interrupted once a threshold or a predetermined value of the patient's absolute blood volume has been detected or calculated: The patient's absolute blood volume at the beginning of the treatment session is known as BV_start=BV_0+OH/K_Guyton. In the following example, BV_start is 5.0 L. Now, the relative blood volume determined by, e.g., a blood volume monitor several times during the treatment is multiplied with BV_start. Once the relative blood volume (in %) has fallen to 95%, the absolute blood volume may be calculated as 5.0 L*0.95=4.75 L.

It may be desired that the blood treatment has to be terminated once the absolute blood volume has fallen under a threshold of, e.g., 4.0 L. That way, the relative blood volume is taken into account during the blood treatment session. Of course, the threshold may be set for each patient and/or treatment session individually.

Of course, what has been explained above with regard to the approximation or prediction of a tolerated relative blood volume during blood treatment may in certain embodiments also be true for the absolute blood volume. In other words, by means of the present invention it may be possible to approximate or predict also an absolute blood volume that is still tolerated. Such a tolerated absolute end blood volume BV_end may be obtained by multiplying BV_start with RBV_predicted.

Therefore, what has been said above with regard to the present invention in the light of a relative blood volume is in many embodiments also true for an absolute blood volume.

What is claimed:

1. A blood treatment device for treating a patient by dialysis, the blood treatment device comprising a controller configured to control the blood treatment device based on: (i) a computer-implemented method for calculating a value representing a refilling volume ($V_{\_refill}$) of the patient that may be observed or found during or due to a blood treatment session of the patient and (ii) relative blood volume (RBV) measurements of the patient that are measured and communicated to the controller during the blood treatment session of the patient, wherein a target range of a relative blood volume ($RBV_{\_end}$) of the patient to be achieved by the blood treatment session is set by the controller based on the refilling volume ($V_{\_refill}$) of the patient, wherein the refilling volume ($V_{\_refill}$) of the patient is determined by the controller using an equation:

$V_{\_refill} = a*UFV + b*(UFR/Hb_{start}) + c*OH + d$ or $V_{\_refill} = a*UFV/Hb + b*OH + c$ wherein:
 a, b, c, and d are parameters;
 $Hb_{\_start}$ is a haemoglobin concentration of the patient at a beginning of the blood treatment session;
 Hb is a haemoglobin concentration of the patient;
 UFV is an ultrafiltration volume;
 UFR is an ultrafiltration rate; and
 OH is the patient's overhydration when beginning the blood treatment session, wherein the controller is configured to adjust the ultrafiltration rate (UFR) during the blood treatment session such that, once the relative blood volume (RBV) measurements of the patient meet the target range of the relative blood volume ($RBV_{\_end}$) that was set by the controller based on the refilling volume ($V_{\_refill}$) of the patient determined by the controller, the relative blood volume (RBV) measurements of the patient do not drop below the target range of the relative blood volume ($RBV_{\_end}$).

2. The blood treatment device according to claim 1, wherein the controller is configured to determine a relative blood volume (RBV) or the refilling volume ($V_{\_refill}$) using an absolute start blood volume ($BV_{\_start}$) upon or before beginning of the blood treatment session.

3. The blood treatment device according to claim 2, wherein the controller is configured to determine the absolute start blood volume ($BV_{\_start}$) using at least one value reflecting a lean mass (LTM) of the patient's body and at least one value reflecting a fat mass (ATM) of the patient's body, or approximations thereof.

4. The blood treatment device according to claim 2, wherein the controller is configured to predict an end value of the relative blood volume (RBV) to be arrived at by an end of the blood treatment session without having caused intradialytic morbid events.

5. The blood treatment device according to claim 2, wherein a time a certain future blood treatment session lasts is calculated or optimized by taking the relative blood volume (RBV) or an end value of the relative blood volume (RBV) into account.

6. The blood treatment device according to claim 2, wherein the controller is configured to adjust the determined relative blood volume (RBV) based on the patient's overhydration (OH) level to be a normalized or normohydrated relative blood volume ($RBV_{\_normohyd}$, or $BV(t)/BV_{\_0}$).

7. The blood treatment device according to claim 1, wherein the controller is configured to determine a normalized or normohydrated relative blood volume ($RBV_{\_normohyd}$) using an equation:

$$RBV_{\_normohyd}(t) = \frac{BV_{\_absolut\_startDialysis}}{BV_{\_0}} * RBV_{\_prior}(t) = \frac{BV_0 + \frac{OH}{K_{\_Guyton}}}{BV_{\_0}} * RBV_{\_prior}(t)$$

wherein:
 $BV_{\_absolute\_startDialysis}$ is an absolute blood volume at the beginning of the blood treatment session;
 $K_{\_Guyton}$ indicates what portion of overhydration is comprised within a vessel system of the patient;
 OH is an overhydration of the patient at the beginning of the blood treatment session;

$RBV\_prior(t)$ is a relative blood volume of the patient as $$\frac{BV(t)}{BV_{absolute\_startDialysis}};$$

with BV(t) being a blood volume of the patient at time point (t); and $BV_0$ is a normohydrated blood volume of the patient at the beginning of the blood treatment session, with $BV_0$ being $BV_{absolute\_startDialysis}$ minus the overhydration (OH) of the patient comprised within the vessel system of the patient.

8. The blood treatment device according to claim 1, further comprising an output device for outputting results of the computer-implemented method.

9. The blood treatment device according to claim 7, wherein the controller is configured to control the blood treatment device in relation to a value or target range representing the relative blood volume (RBV) of the patient or the normalized or the normohydrated blood volume ($RBV\_normohyd$) of the patient.

10. The blood treatment device according to claim 1, the controller being configured to control the blood treatment device in relation to a value or target range representing a target relative blood volume (RBV), wherein the target range is defined by a target overhydration status.

11. The blood treatment device according to claim 1, the controller being configured to control the blood treatment device such that the blood treatment session is terminated or interrupted once an end value of the relative blood volume (RBV) is measured or calculated that has been predicted as an end value or target range of the relative blood volume (RBV) at which the patient has not suffered intradialytic morbid events.

12. The blood treatment device according to claim 1, the controller being configured to control the blood treatment device such that the blood treatment session is terminated or interrupted once a threshold or a predetermined value of the patient's absolute blood volume has been detected or calculated.

13. The blood treatment device according to claim 1, the controller being configured to control the blood treatment device such that the blood treatment session is terminated or interrupted once a threshold or a predetermined value of the absolute blood volume of the patient has been detected or calculated, wherein the absolute blood volume of the patient is determined during the blood treatment session by taking the relative blood volume (RBV) of the patient determined during the blood treatment session into account.

14. The blood treatment device according to claim 1, wherein the blood treatment device is configured for treating the patient by haemofiltration, ultrafiltration, and/or haemodialysis.

* * * * *

UNITED STATES PATENT AND TRADEMARK OFFICE
CERTIFICATE OF CORRECTION

PATENT NO. : 11,676,712 B2
APPLICATION NO. : 16/568595
DATED : June 13, 2023
INVENTOR(S) : Ulrich Moissl et al.

Page 1 of 1

It is certified that error appears in the above-identified patent and that said Letters Patent is hereby corrected as shown below:

In the Claims

Column 15, Line 64, in Claim 1, delete "(UFR/Hb$_{start}$)" and insert --(UFR/Hb$_{\_start}$)--.

Column 17, Lines 4-5, in Claim 7, delete "BV(t)/BV $_{absolute\_startDialysis}$;" and insert --BV(t)/BV$_{\_absolute\_startDialysis}$;--.

Signed and Sealed this
Twenty-ninth Day of August, 2023

Katherine Kelly Vidal
*Director of the United States Patent and Trademark Office*